(12) United States Patent
Brandon et al.

(10) Patent No.: US 11,707,718 B2
(45) Date of Patent: Jul. 25, 2023

(54) SYSTEM FOR CUSTOMIZATION OF COSMETICS

(71) Applicant: Blee.LLC, Nashville, TN (US)

(72) Inventors: Charles C. Brandon, Nashville, TN (US); Travis Floyd, Collierville, TN (US); Peter Phillips, Memphis, TN (US); Phil Powers, Germantown, TN (US)

(73) Assignee: Blee, LLC, Collierville, TN (US)

( * ) Notice: Subject to any disclaimer, the term of this patent is extended or adjusted under 35 U.S.C. 154(b) by 639 days.

(21) Appl. No.: 16/887,030

(22) Filed: May 29, 2020

(65) Prior Publication Data

US 2020/0289998 A1    Sep. 17, 2020

Related U.S. Application Data

(63) Continuation of application No. 16/535,456, filed on Aug. 8, 2019, now Pat. No. 10,814,296, which is a (Continued)

(51) Int. Cl.
*B01F 33/00* (2022.01)
*B01F 33/84* (2022.01)
(Continued)

(52) U.S. Cl.
CPC ........ *B01F 33/8442* (2022.01); *A45D 44/005* (2013.01); *A61K 8/0216* (2013.01); *A61K 8/25* (2013.01); *A61K 8/29* (2013.01); *A61K 8/362* (2013.01); *A61K 8/72* (2013.01); *A61K 8/731* (2013.01); *A61K 8/8111* (2013.01); *A61K 8/8117* (2013.01); *A61K 8/922* (2013.01); *A61K 8/925* (2013.01); *A61K 8/927* (2013.01); *A61K 8/965* (2013.01); *A61Q 1/04* (2013.01); (Continued)

(58) Field of Classification Search
CPC ..... A45D 44/005; A61K 8/922; B01F 33/848; A61Q 3/02
See application file for complete search history.

(56) References Cited

U.S. PATENT DOCUMENTS

| 4,871,262 | A | 10/1989 | Krauss et al. |
| 5,163,010 | A | 11/1992 | Klein et al. |

(Continued)

FOREIGN PATENT DOCUMENTS

| WO | 8907294 A1 | 8/1989 |
| WO | 1998030189 A2 | 7/1998 |
| WO | 2017006018 A1 | 1/2017 |

OTHER PUBLICATIONS

PCT written opinion, PCT/US18/43477 dated Nov. 6, 2018.

*Primary Examiner* — Anshu Bhatia
(74) *Attorney, Agent, or Firm* — Susan Fentress; Veritay Group IP PLLC

(57) ABSTRACT

The presently disclosed subject matter relates to a system for customizing a cosmetic product. The system includes: an interface device, in electronic communication with a single batch formulation device. The single batch formulation device is configured to formulate a customized cosmetic product, and a threaded container configured to be imported into the single batch formulation device containing a base and exported from the single batch formulation device containing the customized cosmetic.

10 Claims, 15 Drawing Sheets

Related U.S. Application Data continuation of application No. PCT/US2018/043477, filed on Jul. 24, 2018.

(60) Provisional application No. 62/536,621, filed on Jul. 25, 2017.

(51) Int. Cl.

| | | |
|---|---|---|
| *A61K 8/02* | (2006.01) | |
| *A61K 8/25* | (2006.01) | |
| *A61K 8/72* | (2006.01) | |
| *A61K 8/73* | (2006.01) | |
| *A61Q 1/06* | (2006.01) | |
| *A61Q 1/12* | (2006.01) | |
| *A61Q 3/02* | (2006.01) | |
| *A45D 44/00* | (2006.01) | |
| *A61K 8/29* | (2006.01) | |
| *A61K 8/362* | (2006.01) | |
| *A61K 8/81* | (2006.01) | |
| *A61K 8/92* | (2006.01) | |
| *A61K 8/96* | (2006.01) | |
| *A61Q 1/04* | (2006.01) | |
| *B01F 27/93* | (2022.01) | |
| *B01F 35/45* | (2022.01) | |
| *B01F 35/71* | (2022.01) | |
| *B01F 101/21* | (2022.01) | |

(52) U.S. Cl.
CPC .............. *A61Q 1/06* (2013.01); *A61Q 1/12* (2013.01); *A61Q 3/02* (2013.01); *B01F 27/93* (2022.01); *B01F 33/848* (2022.01); *B01F 35/4521* (2022.01); *B01F 35/717611* (2022.01); *B01F 2101/21* (2022.01)

(56) References Cited

U.S. PATENT DOCUMENTS

| | | |
|---|---|---|
| 5,547,660 A * | 8/1996 | Seed .................. A61Q 3/02 424/61 |
| 5,622,692 A | 4/1997 | Rigg et al. |
| 5,681,550 A | 10/1997 | Rubino |
| 6,510,366 B1 | 1/2003 | Murray et al. |
| 7,174,310 B2 | 2/2007 | Bartholomew et al. |
| 8,352,070 B2 | 1/2013 | Bartholomew et al. |
| 8,532,736 B1 | 9/2013 | Malzbender et al. |
| 8,596,498 B2 | 12/2013 | Werner et al. |
| 8,666,540 B2 | 3/2014 | Milhorn |
| 8,702,772 B2 | 4/2014 | Luzon et al. |
| 8,709,003 B2 | 4/2014 | Island et al. |
| 8,734,766 B2 * | 5/2014 | Oi ........................ A61K 8/345 424/64 |
| 8,830,468 B2 | 9/2014 | Igarashi |
| 8,880,218 B2 | 11/2014 | Bartholomew et al. |
| 8,884,242 B2 | 11/2014 | Chhibber et al. |
| 8,908,904 B2 | 12/2014 | Santos et al. |
| 8,915,562 B2 | 12/2014 | Edgar et al. |
| 8,933,994 B2 | 1/2015 | Gross et al. |
| 8,974,111 B2 | 3/2015 | Phallen |
| 8,995,760 B2 | 3/2015 | Gill |
| 9,064,180 B2 | 6/2015 | Korichi et al. |
| 9,122,918 B2 | 9/2015 | Howell et al. |
| 9,256,963 B2 | 2/2016 | Cummins et al. |
| 9,449,400 B2 | 9/2016 | Stephan et al. |
| 9,858,685 B2 | 1/2018 | Nichol et al. |
| 2001/0047309 A1 | 11/2001 | Bartholomew et al. |
| 2004/0191192 A1 | 9/2004 | Blankenbeckler et al. |
| 2006/0124196 A1* | 6/2006 | Bartholomew ..... B01F 35/2207 141/100 |
| 2006/0152744 A1 | 7/2006 | Sanger |
| 2006/0239950 A1* | 10/2006 | Mohammadi ........... A61K 8/31 424/74 |
| 2008/0152678 A1 | 6/2008 | Shah et al. |
| 2008/0311061 A1 | 12/2008 | Heuer |
| 2009/0123402 A1 | 5/2009 | Oi |
| 2011/0226803 A1 | 9/2011 | Schwartz |
| 2013/0300919 A1 | 11/2013 | Fletcher et al. |
| 2014/0081463 A1* | 3/2014 | Igarashi ................ G05D 11/00 700/265 |
| 2015/0107678 A1 | 4/2015 | Igarashi |
| 2015/0314141 A1 | 11/2015 | Choi |
| 2015/0315520 A1 | 11/2015 | Eppler et al. |
| 2017/0151538 A1 | 6/2017 | Balooch et al. |
| 2017/0154372 A1 | 6/2017 | Balooch et al. |
| 2018/0085721 A1* | 3/2018 | Rinaldis .................. B01F 29/34 |
| 2019/0321841 A1 | 10/2019 | Kim et al. |

* cited by examiner

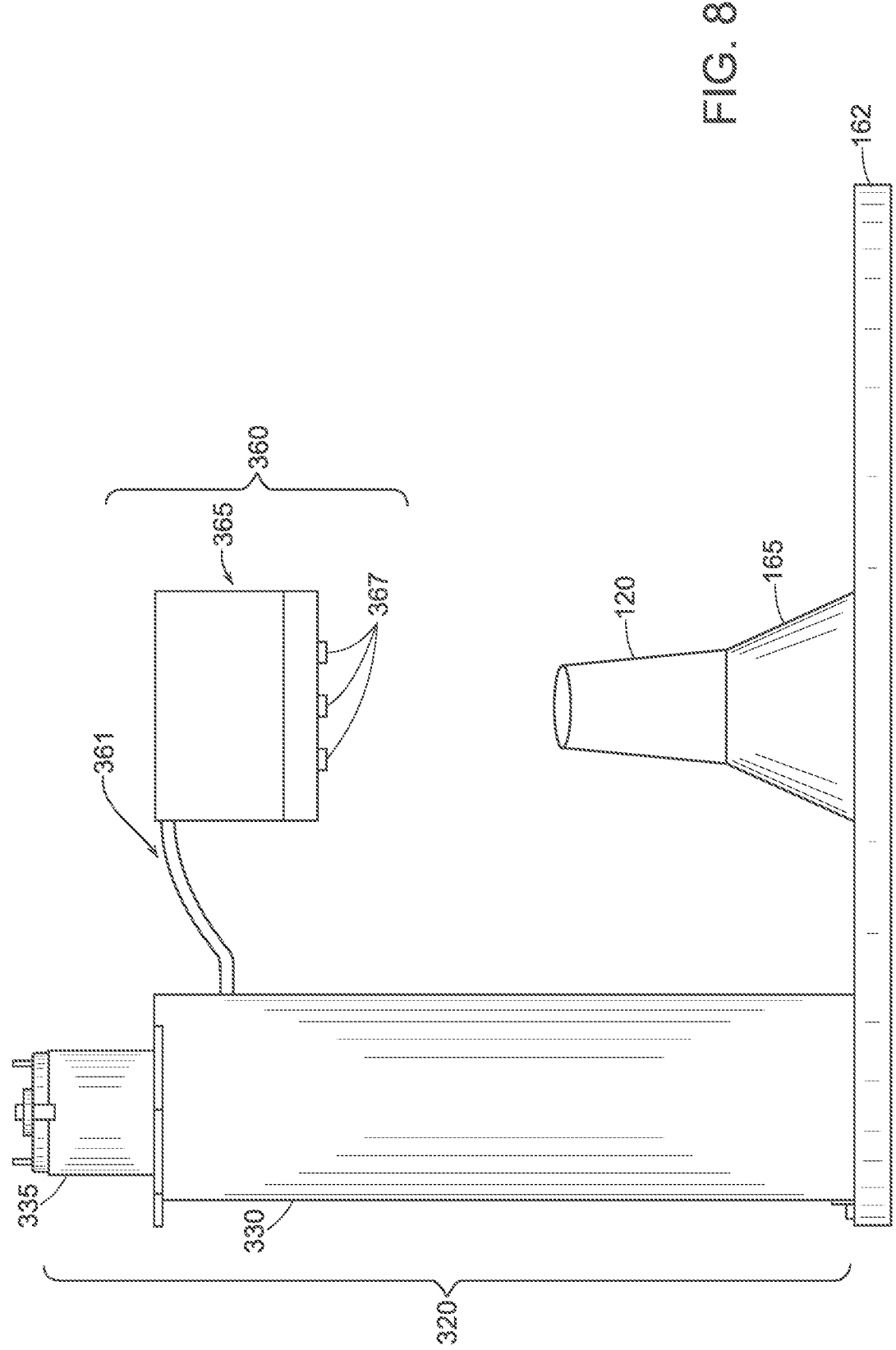

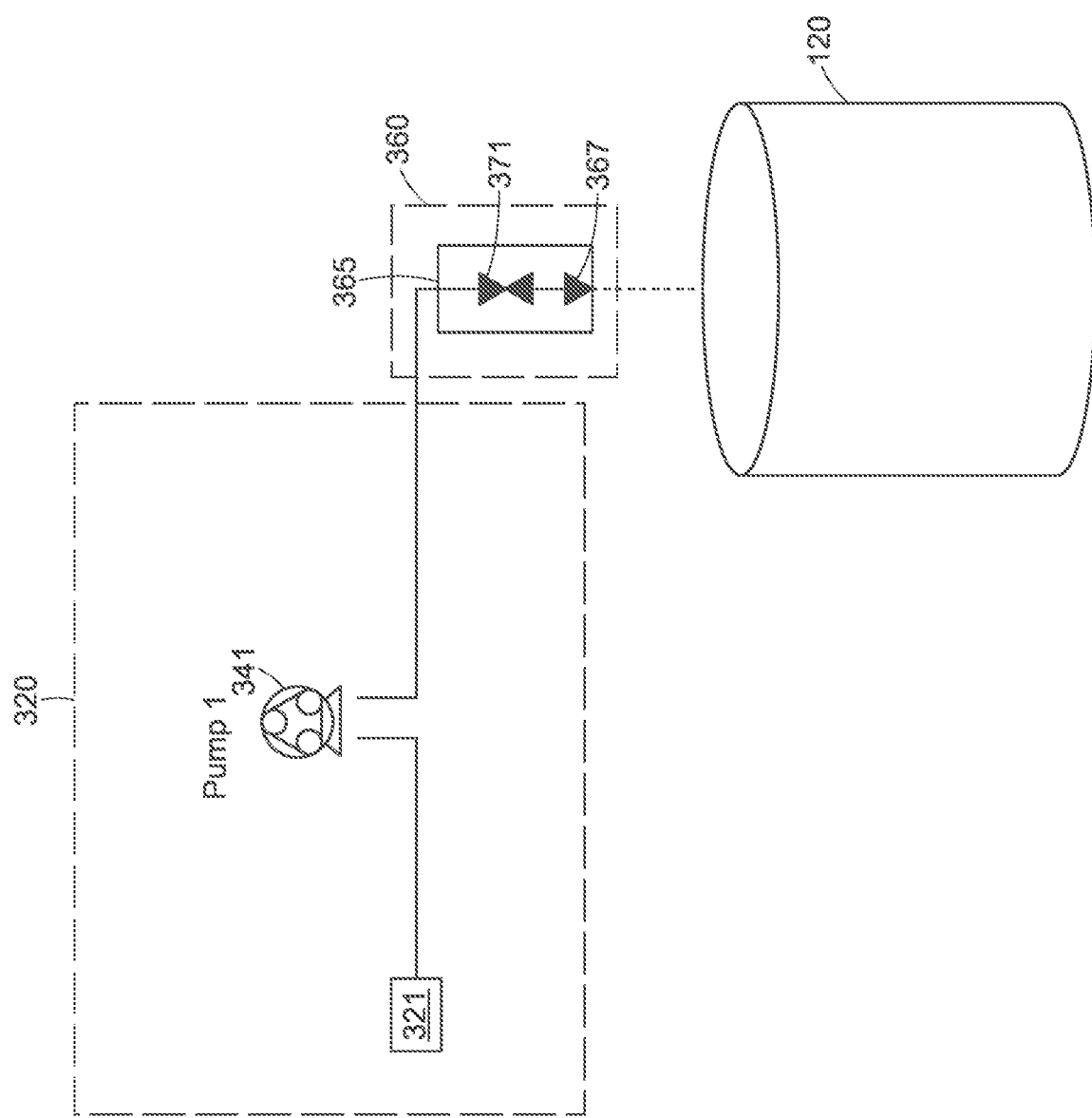

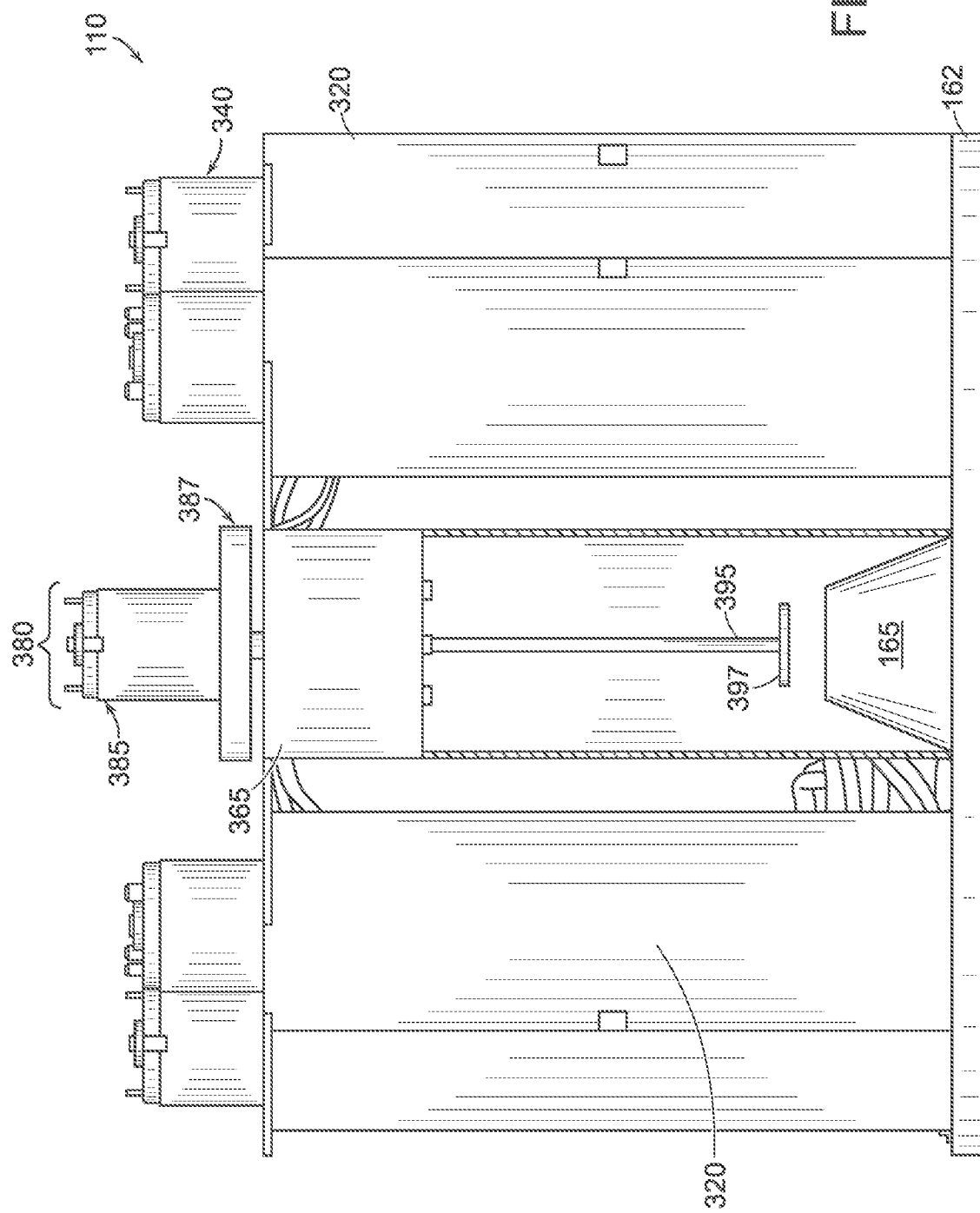

SYSTEM FOR CUSTOMIZATION OF COSMETICS

RELATED APPLICATIONS

This application claims priority to U.S. patent application Ser. No. 16/535,456 filed Aug. 8, 2019; U.S. patent application Ser. No. 16/314,598 filed Dec. 31, 2018 now U.S. Pat. No. 10,625,226, PCT/US18/43477 filed Jul. 24, 2018 U.S. Provisional Patent Application No. 62/536,621, filed Jul. 25, 2017 the entire disclosures of which is hereby incorporated by reference in its entirety.

TECHNICAL FIELD

The presently disclosed subject matter relates to a system and method to customize cosmetics.

BACKGROUND OF THE INVENTION

In the field of custom cosmetics, skin coloration has been measured spectrophotometrically to provide a custom color. A mixing and dispensing device is electronically connected to a processor programmed to provide custom-blended cosmetics in a retail location/environment. In this device, color blenders, bases, thinners, and additives are dispensed via a plurality of nozzles into a container and mixed. Various vibration mixers and shakers are used to mix the required ingredients. However, due to the number of ingredients being mixed and the complexity of the process, this device is only for commercial use. A need exists in the industry to produce a simple machine for in-home use, while still providing users the ability to customize a wide variety of cosmetic products.

SUMMARY OF THE INVENTION

This summary describes several embodiments of the presently disclosed subject matter, and, in many cases, lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

The inventive subject matter of this invention includes: a method to formulate a plurality of types of cosmetic products with color options. The method includes the steps of: inputting a product selection into a graphical user interface, wherein the product selection consists of: nail polish, foundation and lip-gloss; inputting a color selection into the graphical user interface to provide a selected cosmetic product, wherein the graphical user interface is in electronic communication with a single batch formulation device; inserting a threaded container containing a sufficient amount of a base for the selected cosmetic product into the single batch formulation device configured to formulate the plurality of custom cosmetic products, wherein the single batch formulation device is made of a stationary platform on which the selected cosmetic product is formulated; outputting data on the selected cosmetic product to the single batch formulation device, dispensing the selected pigment into the base in the threaded container; and mixing the selected pigment in the threaded container to provide the selected product.

The presently disclosed subject matter relates to a system for formulating a plurality of types of cosmetic products with a color selection. The system in the most basic form is made of: a computer application deployed on an interface device to facilitate product and color selection; a single batch formulation device, wherein the remote interface device electronically communicates with the single batch formulation device, and wherein the remote interface device is configured to input the selection of the type of cosmetic product and the color selection to the single batch cosmetic device; and a plurality of threaded containers, each container of the plurality of threaded containers sized to be imported into the single batch formulation device, and each of the threaded containers containing a base specific for a type of cosmetic product of the plurality of types of cosmetic products; wherein the single batch formulation device is configured to formulate the cosmetic product to the selected color and export the cosmetic product in to one of the plurality of threaded containers. In one embodiment, the single batch formulation device is made of a stationary platform on which the cosmetic product is formulated.

More specifically, the interface device is made of: a display device; a processor; and a memory having an application stored thereon. The interface device is communicatively coupled to the formulation device and wherein the application, when executed by the processor, causes the interface device to: generate a graphical user interface for configuring a plurality of types of cosmetic products, the graphical user interface including a plurality of user input elements, cause the graphical user interface to be displayed by way of the display device, receive, by way of at least one of the plurality of user input elements, an input command corresponding to the at least one of the plurality of user input elements, and transmit, to the single batch formulation device, a message based on the received input command, wherein the single batch formulation device is configured to: receive the message and perform an action in response to receiving the message, and wherein the graphical user interface further includes: a selectable list of cosmetic products and a selectable list of color options, wherein the single batch formulation device commences to formulate a plurality of types of cosmetic products with color options, in response to the inputting of a predetermined user input command.

Another aspect of the inventive subject matter is a single batch formulation device configured to formulate a customized cosmetic product made of: a bottom plate supporting the single batch formulation device; a plurality of pigment assemblies positioned above the bottom plate, wherein each of the pigment assemblies is made of a pigment container connected to a pump and pump motor; wherein the pigment container contains a pigment ingredient correlating with a specific color; a recessed area, wherein the plurality of pigment assemblies are positioned around the recessed area; a dispensing assembly made of a dispensing head and a plurality of dispensing tips, wherein each of the plurality of dispensing tips is in a direct fluid connection with one of the plurality of pigment assemblies; a homogenizer assembly made of a mixing motor connected to a pigment mixing rod, wherein the pigment mixing rod is disposed below the dispensing assembly and the pigment mixing rod is positioned within the recessed area; a stationary platform positioned within the recessed area, wherein the pigment mixing rod is of sufficient length to contact a base product contained in a container positioned on the stationary platform; and a micro-controller configured to control the operations of the single batch formulation device.

Advantages of the presently disclosed subject matter will become evident to those of ordinary skill in the art after a study of the description, Figures, and non-limiting Examples in this document.

BRIEF DESCRIPTION OF THE DRAWINGS

FIG. 8 is a side-view of a one of the plurality of the pigment assemblies and the dispensing assembly.
FIG. 9B is a fluid flow diagram
FIG. 10 is a view of device showing the homogenizer elements of an embodiment of the single batch formulation device.

DESCRIPTION OF EXEMPLARY EMBODIMENTS

The present invention can be understood more readily by reference to the following detailed description of the invention. It is to be understood that this invention is not limited to the specific devices, methods, conditions or parameters described herein, and that the terminology used herein is for describing embodiments by way of example only and is not intended to be limiting of the claimed invention. Also, as used in the specification including the appended claims, the singular forms "a," "an," and "the" include the plural, and reference to a numerical value includes at least that value, unless the context clearly dictates otherwise. Ranges can be expressed herein as from "about" or "approximately" one value and/or to "about" or "approximately" another value. When such a range is expressed, another embodiment includes from the one value and/or to the other value. Similarly, when values are expressed as approximations, by use of the antecedent "about," it will be understood that the value forms another embodiment. All combinations of method or process steps as used herein can be performed in any order, unless otherwise specified or clearly implied to the contrary by the context in which the referenced combination is made.

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the inventions and are not restrictive of the invention as claimed. Unless defined otherwise, all technical and scientific terms used herein have the same meaning as commonly understood by one of ordinary skill in the art to which this invention belongs.

Figure 1:
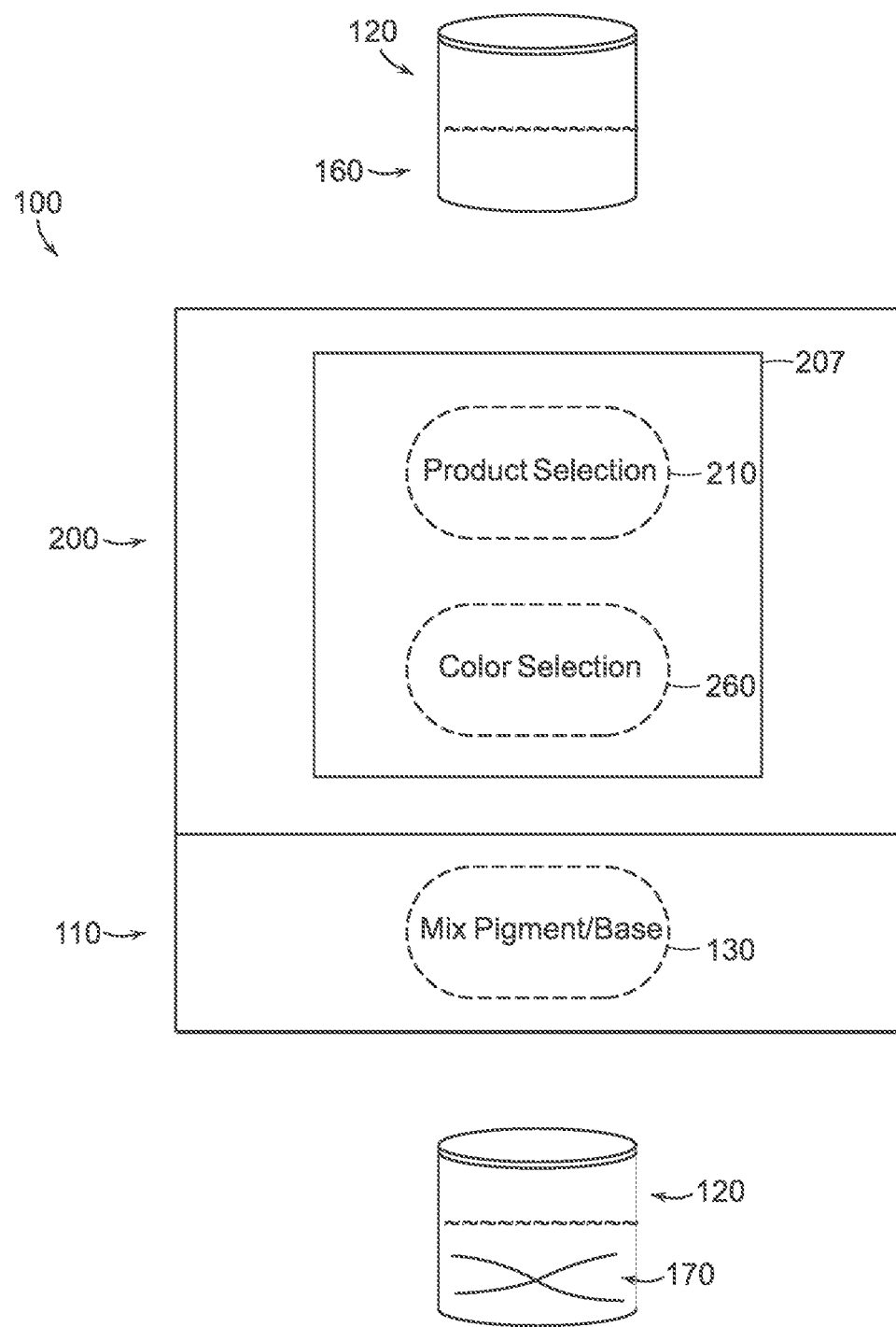
FIG. 1 is an overview of the system.
Figure 2:
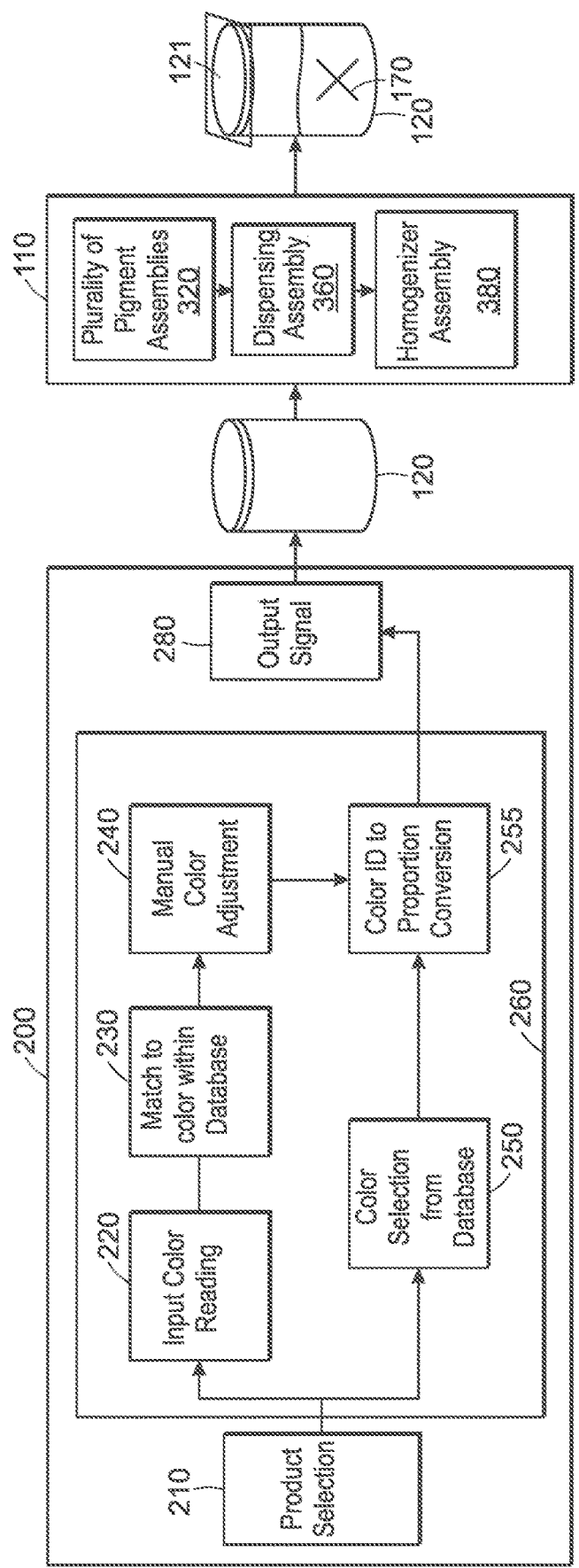
FIG. 2 is a more detailed overview of the system.

Now referring to FIGS. 1-2, a system 100 for the automated delivery of customized cosmetics as a single batch is shown. The system 100 has three components: a computer application 207 deployed on remote interface device 200 for product and color selection, a single batch formulation device 110, and a threaded container 120 containing a base product 160. A single batch formulation device 110 is configured to process a single batch of the desired cosmetic. Single-batch cosmetics refer to individual units of a base product ready to be customized by a user. The user customizes product selection 210 and color selection 260 via the remote interface device 200 with the computer application 207. The same threaded container 120 with the customized cosmetic product 170 is removed from the single batch formulation device 110.

In a preferred embodiment of the invention, color can be selected in two ways. First, the user can select a color from a database 250 of colors. Second, the user can match a color read from an input 220 such as from a picture or photographic image. The user can match a color from an inputted image to a color within the database 230. The step of color matching involves providing the computer application 207 with an image to extract color information, wherein the extraction step involves picking a color from the image and identifying the color proportion value. Once a color is finalized the representative proportion value of the color is identified 255 and electronically communicated 280 to the single batch formulation device 110.

The single batch formulation device 110 has the operational mode of mixing the pigment and the base 130. The single batch formulation device 110 can provide a liquid-based or gel-based cosmetic including but not limited to: foundation, lip gloss, and nail polish of a specified shade or composition. A threaded container 120 containing a base product 160 for a specified cosmetic is inserted into a single batch formulation device 110 for each cosmetic product that is desired. Each threaded container 120 is sized to be imported into the single batch formulation device 110. Each of the threaded containers 120 contain a base specific for a type of cosmetic product of the plurality of types of cosmetic products. Precise amounts of pigment are dispensed from a plurality of pigment assemblies 320 according to the color identified or selected using the remote interface device 200 into the threaded container 120 by the dispensing assembly 360. A homogenizer assembly 380 mixes the final product directly in each of the threaded containers 120. The threaded containers 120 can be sealed with a lid or cap 121 to retain the formulated cosmetic 170 with in the threaded container 120.

Figure 3:
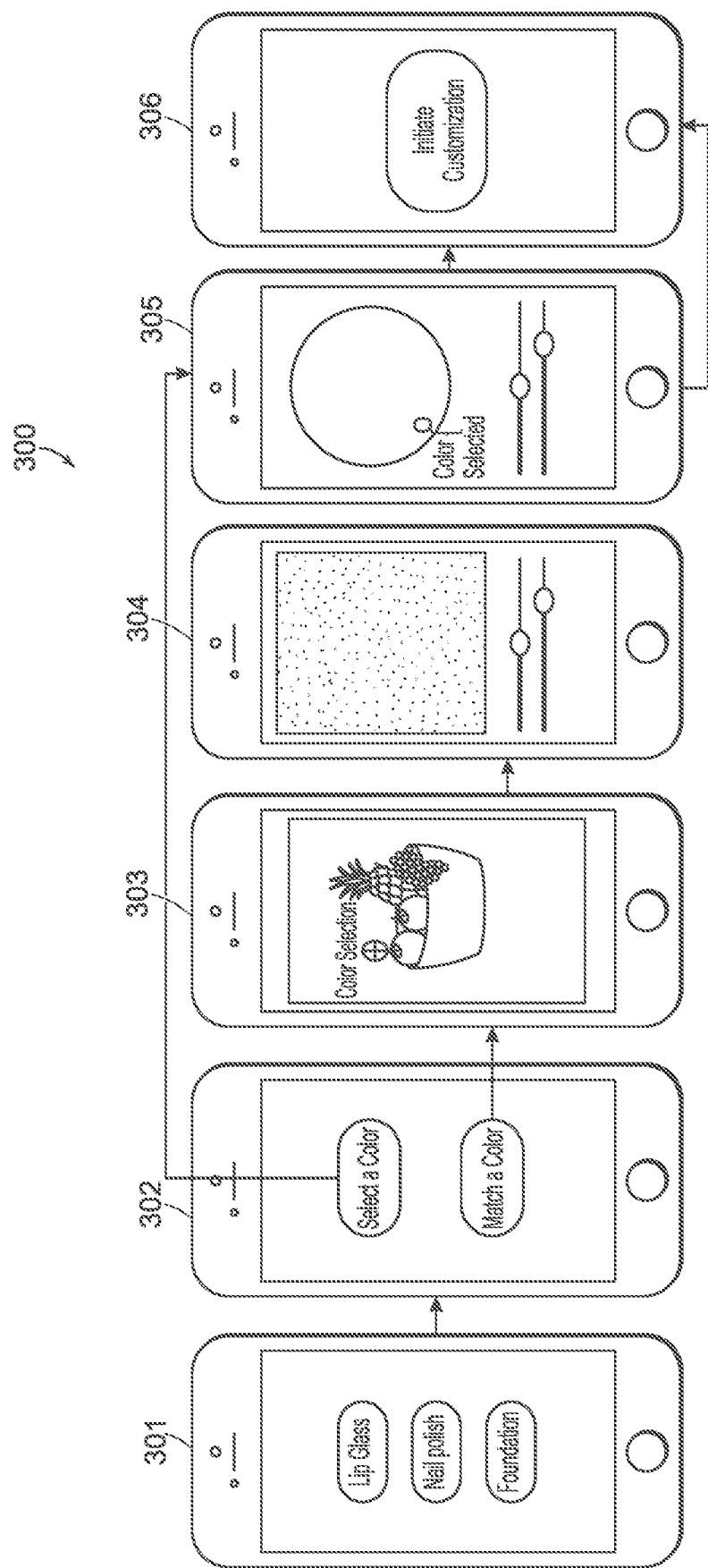
FIG. 3 is a view of a graphical user interface.

Now referring to FIG. 3, a view of the graphical user interface 300 that allows a user to make selections on a remote interface device 200 that are communicated to the single batch formulation device 110. The graphical user interface 300 includes a plurality of screens: a first product selection screen 301 for the user to select one of lip gloss, nail polish, foundation, or similar products. Once a product has been selected, a second screen 302 prompts a user to select or match a color. Selecting a color prompts the user to a color selection screen 305 where the user selects a color from a database of colors, such as from a color wheel with sliding bars to adjust color values.

Matching a color prompts the user to provide an image with a desired color for the remote interface device 200 to match. An image with the desired color is taken with or uploaded to the remote interface device 200. A color can be extracted from the image and the pixel data converted into proportions of red, green, and blue colors that can be processed by a processor. Color pixel classification applications have been commercially developed and are available for use. In an alternative embodiment, with a color pixel classification application on the remote interface device 200, such as a cell phone, the color of the sample is matched to a color within the color database. For example, skin tone can be determined using one of several available color matching apps. Once chosen, the user can adjust the color values 304 as desired. The color is matched to a color within the color database 305. Once the desired color is selected, a final screen 306 prompts the user to initiate customization, sending the information to the single batch formulation device 110.

Figure 4:
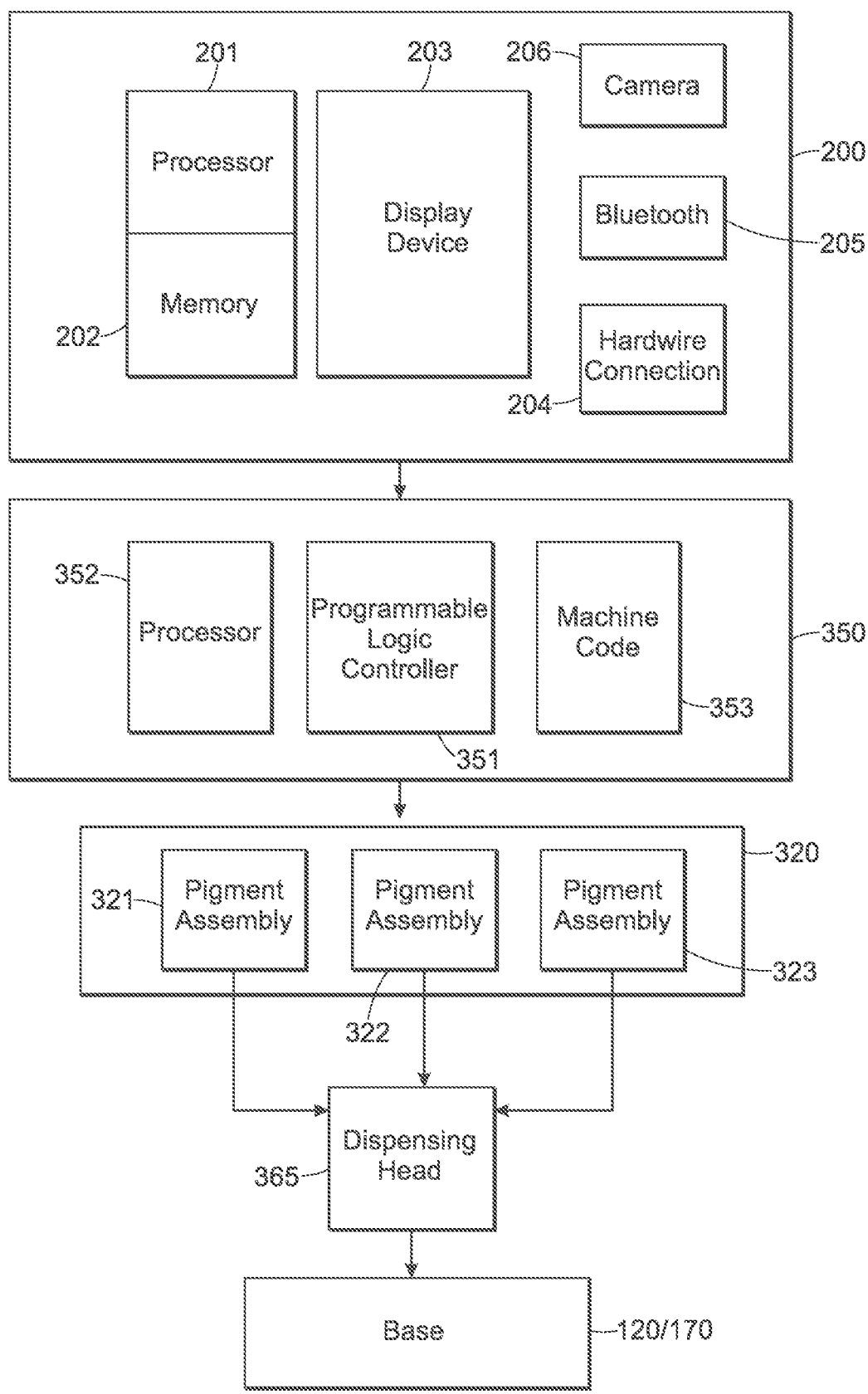
FIG. 4 is a block diagram of assemblies of the interface device and single batch formulation device.

Now referring to FIG. 4, a block diagram of assemblies of an embodiment of the present invention representing the interface device and single batch formulation device. The remote interface device 200 includes a processor 201 with memory 202 capable of running a computer application 207 for a user to make product and color selections. The remote interface device 200 also includes a display device 203 through which the user makes selections. This could be a touch screen if the remote interface device 200 were a smartphone or tablet. Other interfaces could be a mouse and keyboard, with which the user makes product and color selections in accordance with the graphical user interface 300 described in FIG. 3.

The remote interface device 200 can include non-transitory memory (not shown) for storing frequently used product and color selections. The remote interface device 200 can include a port for a hardwire connection 204 such that the remote interface device 200 could be connected to an external device to send instructions to the external device (not shown). The remote interface device 200 can also connect to the formulation device by Bluetooth 205 connection. The remote interface device 200 can include a camera 206 for color matching. The computer application 207 needs access to the camera 206 to take pictures within the app for color matching. Once the user initiates customization in the graphical user interface 300 on the remote interface device 200, as described in FIG. 3, instructions, written in a high-level language (such as Java, C, or Swift), are compiled by the computer application 207 on the remote interface device 200. Instructions are then sent by a means, such as Bluetooth 205 or by a hardwire 204 connection, to a programmable logic controller inside a microcontroller 350 stored in the single batch formulation device 110. Instructions are received by the programmable logic controller 351 by a means such as by a hardwire connection, Bluetooth, or other wireless connection. Once received by the programmable logic controller 351, instructions are assembled into machine code 353 and are sent to the processor 352 of the single batch formulation device 110. The processor 352 receives machine code 353 from the programmable logic controller 351 and issues instructions to the programmable logic controller 351. Instructions specify how much of each provided pigment housed in the plurality of pigment assemblies 320 is required to create the desired color which is delivered through dispensing head 365 to the base product 120/170 and mixed to completion.

Figure 5:
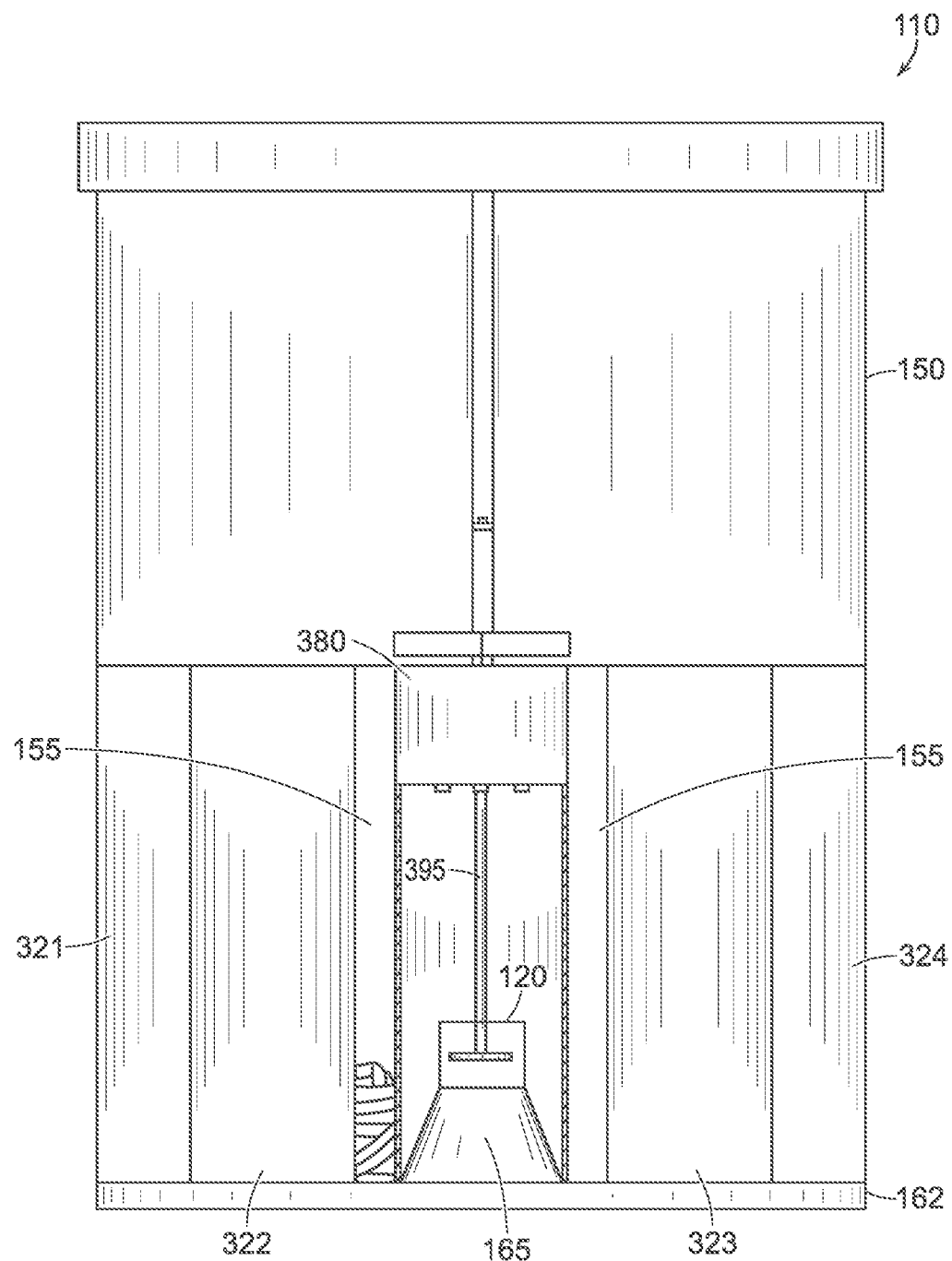
FIG. 5 is a front isometric view of a rendering of an embodiment of the single batch formulation device.

FIG. 5 shows a front view of an embodiment of the single batch formulation device 110. The single batch formulation device 110 is partially enclosed in a circuit housing 150. The circuit housing 150 is shown to completely encase all electronic components and circuitry including motors, relays and the microcontroller (not shown in this view). Positioned below the circuit housing 150 is the plurality of pigment assemblies 320 (shown individually as 321, 322, 323 and 324) and a portion of the homogenizer assembly 380 is shown.

Each of the pigment assemblies are specific for a specific color. Four are shown for example. The color distribution of pigments in a variety of cosmetic products is shown. Based on this distribution, a combination of six of the pigments can approximate most shades. These six pigments can include: Blue 1: CI 42090, Yellow Iron Oxide: CI 77492, Red Iron Oxide: CI 77491, Black Iron Oxide: CI 77499, Red 6 Lake: CI 15850, and Yellow 5 CI 19140. Possible substitutes include Yellow 6, Carmine, Red 4, Red 7, Red 27, Red 28, Red 30, Red 33, Manganese Violet, Mica-derived pigments, etc. Due to the container nature of the pigment containers, users can curate which pigments best suit their needs.

The plurality of pigment assemblies 320 are positioned around the recessed area 155. Several structural components are in the recessed area 155. The homogenizer assembly 380 is made of a mixing motor 385 connected to a pigment mixing rod 395. A stationary platform 165 is positioned co-radially with the pigment mixing rod 395. The stationary platform 165 is sized to hold the threaded container 120 when base product is placed into the single batch formulation device 110 for tinting into a specified color. In one embodiment, the stationary platform 165 has a trapezoidal cross-section that is fully revolved. The single batch formulation device 110 is supported on a bottom plate 162. In this exemplary embodiment, the bottom plate 162 is generally cylindrical.

Figure 6:
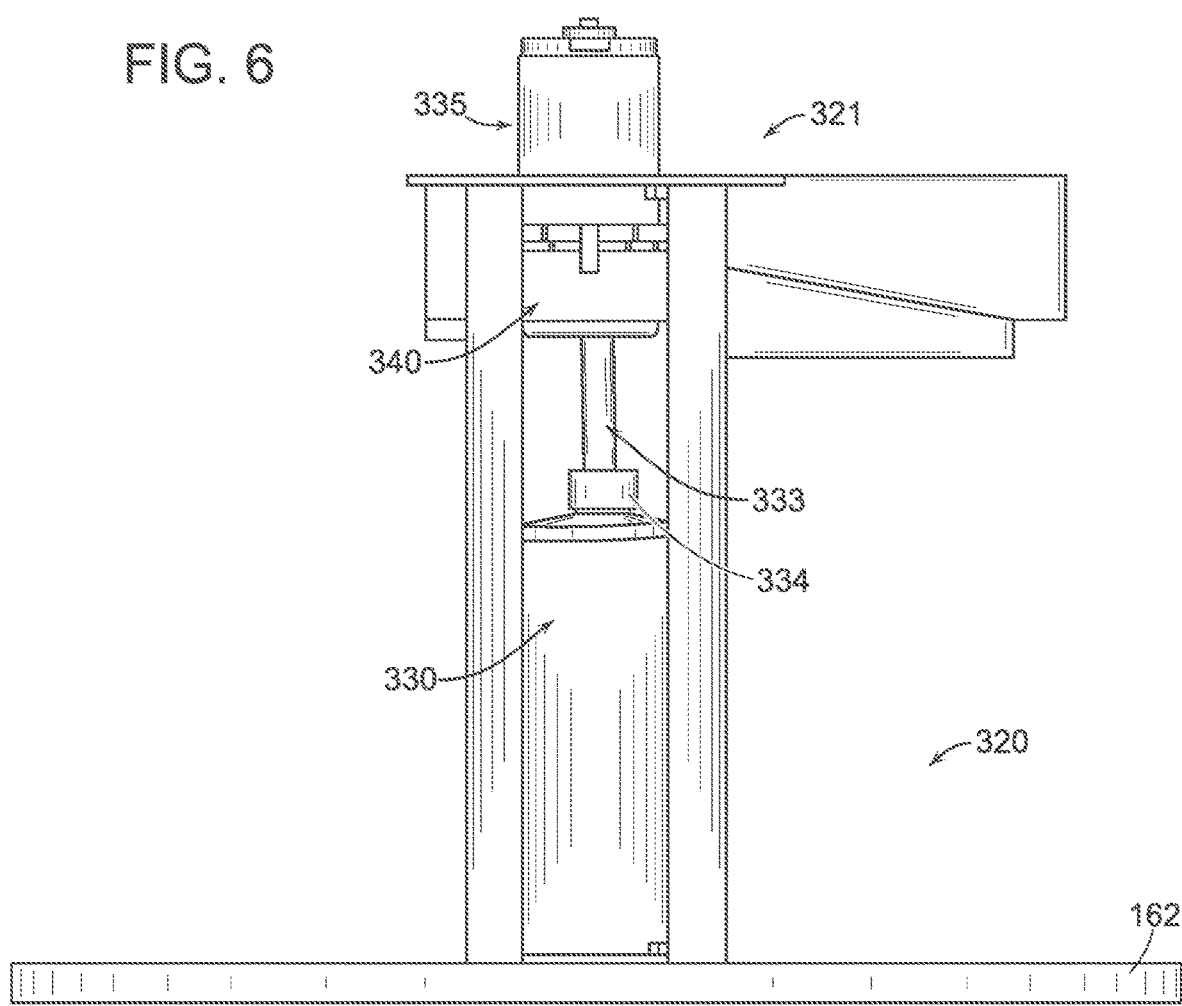
FIG. 6 is a view of one of the plurality of the pigment assemblies.

FIG. 6 shows a pigment assembly 321 of the plurality of pigment assemblies 320. All of the pigment assembly 321 of the plurality of pigment assemblies 320 have the same components and configurations. Only pigment assembly 321 is shown for illustration. A pigment container 330 is configured to hold a specific liquid pigment and can be for example a disposable bottle or container. The structure of the pigment container 330 is a thin-walled cylindrical shaft that is terminated on the bottom by a plate 162 and at the top by the tubing 333. The pigment container 330 is replaceable and attaches to tubing 333 with a connected tip 334. The tubing 333 connects to pump 340 and is used as a way to transport the pigment coloring to the dispensing head 365.

In one illustrative example, the peristaltic pump 340 has torque transferred to it via a drive shaft 331 driven direct by a motor 335 or with a gearbox as an added stage to multiply torque and reduce speed (not shown). A variety of motors 335, including three phase DC brushless or single-phase DC brushed motors, can be used. Using the provided torque, the peristaltic pump 340 can by means of peristalsis create low pressure in the pigment bottle and relative high pressure on the other side of the peristaltic pump 340. This pressure gradient drives the pigment through the tubing 333. It should be noted that this is a view of one of the pigment assembly 321 of the plurality of pigment assemblies 320. Each specific color has its own designated pigment assembly 321 of the plurality of pigment assemblies 320.

Figure 7:
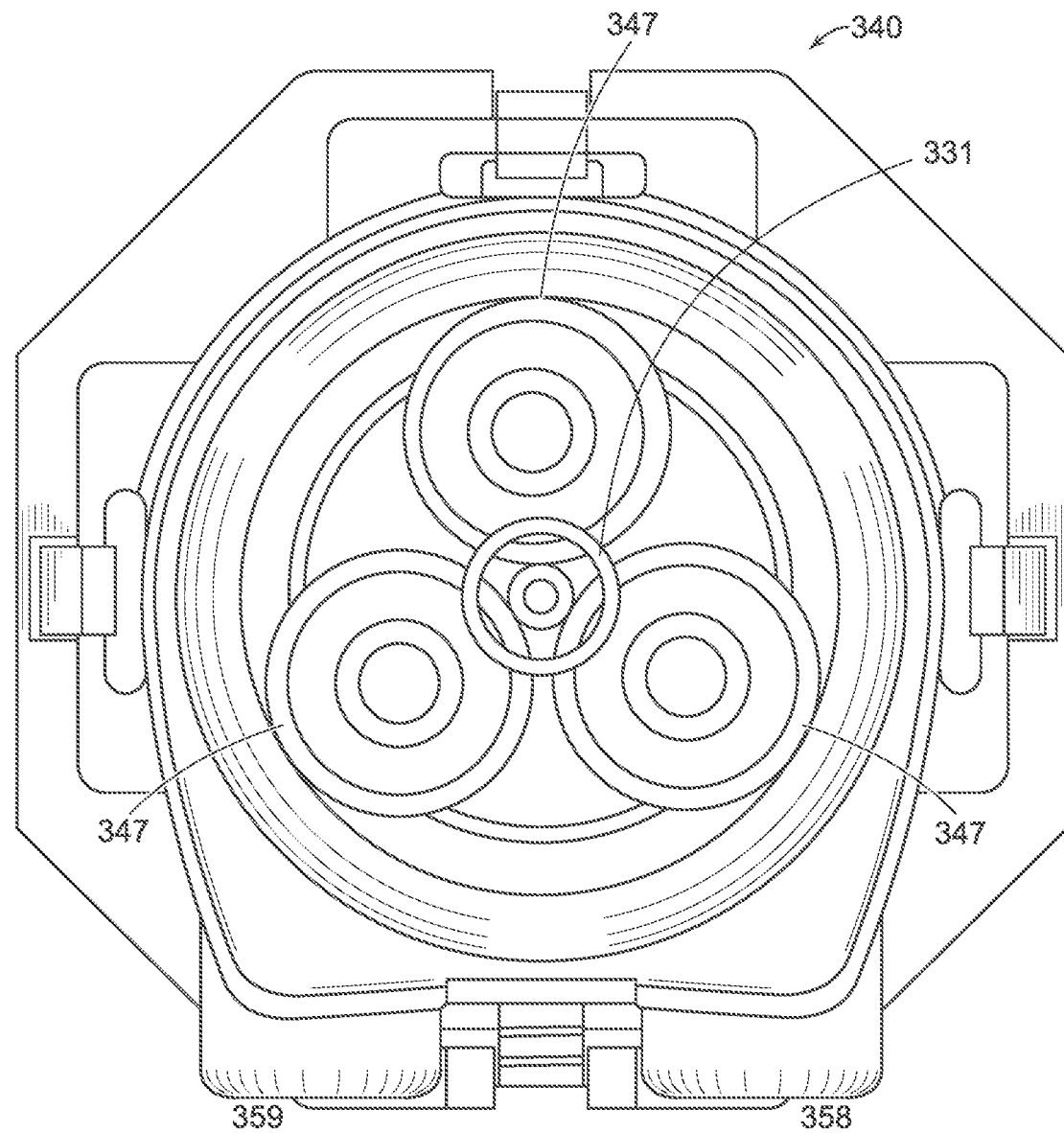
FIG. 7 is a cross-sectional view of FIG. 6.

FIG. 7 is a cross section view of a peristaltic pump 340. It shows the inlet and outlet path for the tube and how the plurality of rollers 347 squeeze a section of the tube. The inlet 358 is where tubing 333 from the pigment container 330 goes into the peristaltic pump 340. The outlet 359 is where the tubing 361 leaves the peristaltic pump 340 to connect with the dispensing assembly 360.

Figure 9A:
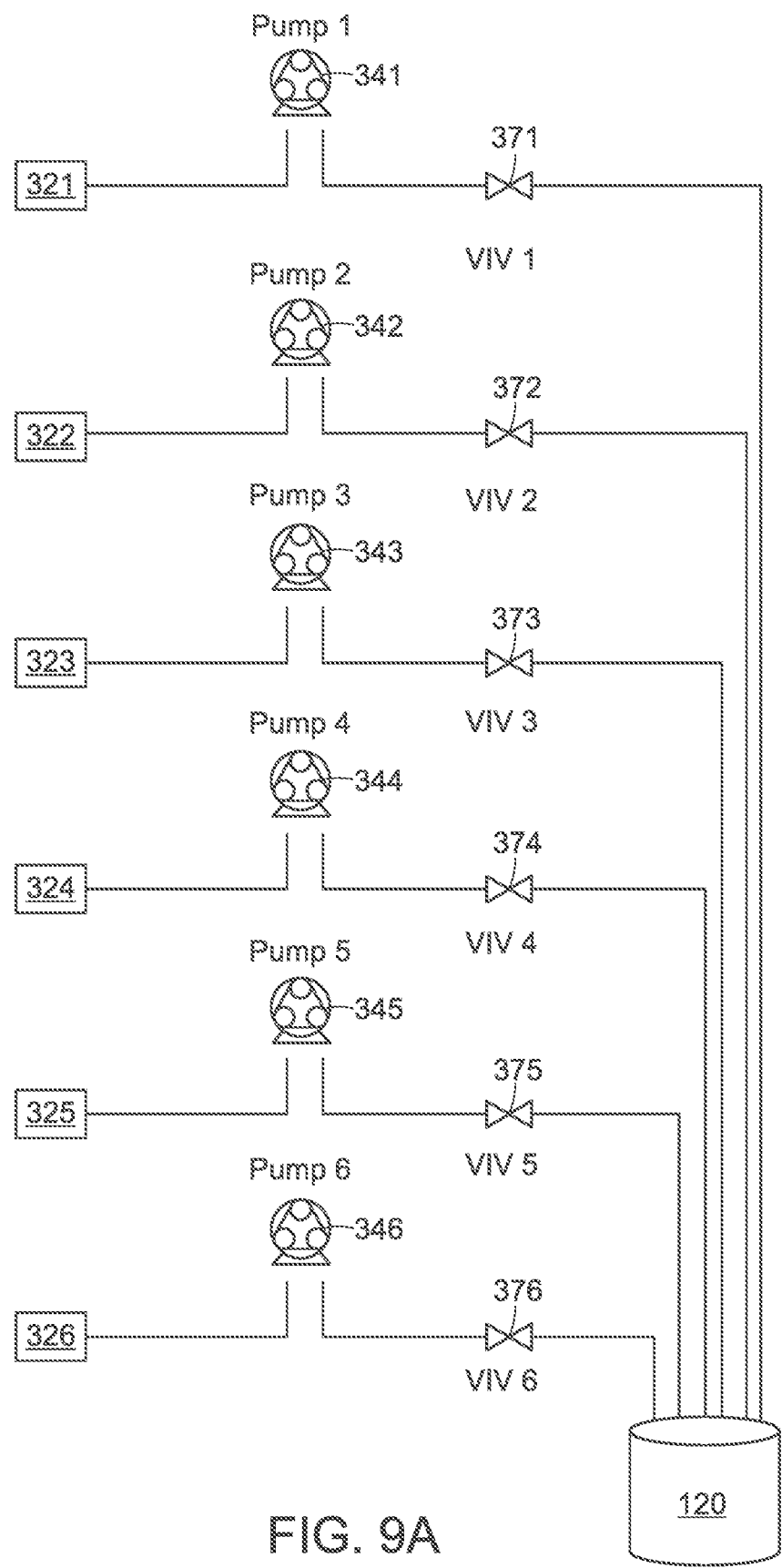
FIG. 9A is a fluid flow diagram

FIGS. 8 and 9A and 9B show one of the plurality of the pigment assemblies 320 and the dispensing assembly 360. It should be noted that there are a number of pigment assemblies 320, each containing a different pigment in the assembly. Each of the plurality of pigment assemblies 320 is made of a pigment container 320 connected to a pump 340 and pump motor 335. Each of the pigment assemblies 320 has a direct fluid connection with the dispensing assembly 360. The dispensing assembly 360 is made of a dispensing head 365 and a plurality of dispensing tips 367 wherein each of the plurality of dispensing tips 367 is in a direct fluid connection with one of the plurality of pigment assemblies 320.

The dispensing assembly 360 is made of a dispensing head 365 and a plurality of dispensing tips 367. The high-pressure pigment effluent flows from the pigment container 330 to the dispensing head 365. The dispensing head 365 can have multiple pigment effluent tubes routing into it. Inside the dispensing head 365 a proportional number of valves 371, 372, 373, 374, 375, and 376 can be provided to help prevent unwanted leakage. Connected to the valves, a proportional number of dispensing tips 367 aimed at the threaded container 120 are provided.

FIGS. 9A-9B show a general instrumentation and process diagram of the system. The process flow takes the pigment from: the plurality of pigment assemblies 320 each having a pigment container 321, 322, 323, 324, 325, and 326 through a corresponding pump 341, 342, 343, 344, 345, and 346 to the dispensing assembly 360. The dispensing assembly 360 includes a dispensing head 365 where it can be terminated by a corresponding valve 371, 372, 373, 374, 375, and 376 and then continued to a plurality of dispensing tips 367, which are in a direct fluid connection with one of the plurality of pigment assemblies 320. It is this direct fluid connect that allows a specific pigment or combination of pigments to be delivered. Between the plurality of dispensing tips 367 and the threaded container 120 is an air gap.

FIG. 10 is a front view of the single batch formulation device 110 showing the homogenizer assembly 380. The homogenizer assembly 380 is made of a mixing motor 385, coupled with a pigment mixing rod 395. The purpose of the homogenizer assembly 380 is to blend the dispensed pigments. In addition, a height adjuster 387 is a protruding tab that is configured for user interface. The mixer height adjuster 387 can be lifted manually, pulling up the pigment mixing rod 395 with it, allowing for removal of the threaded container 120. The mixing motor 385 is rigidly attached to the top of the mixer height adjuster 387 and has a centered-through hole (not shown) providing clearance for the pigment mixing rod 395 to couple with the mixing motor 385 output shaft (not shown) and rotate freely. The pigment mixing rod 395 is held in an upright position with two degrees of freedom by smooth and closely fitting holes (not shown) centered at the top and bottom of the dispensing head 365. These two smooth holes can be substituted by bushings, needle bearings, or ball bearings.

Figure 11:
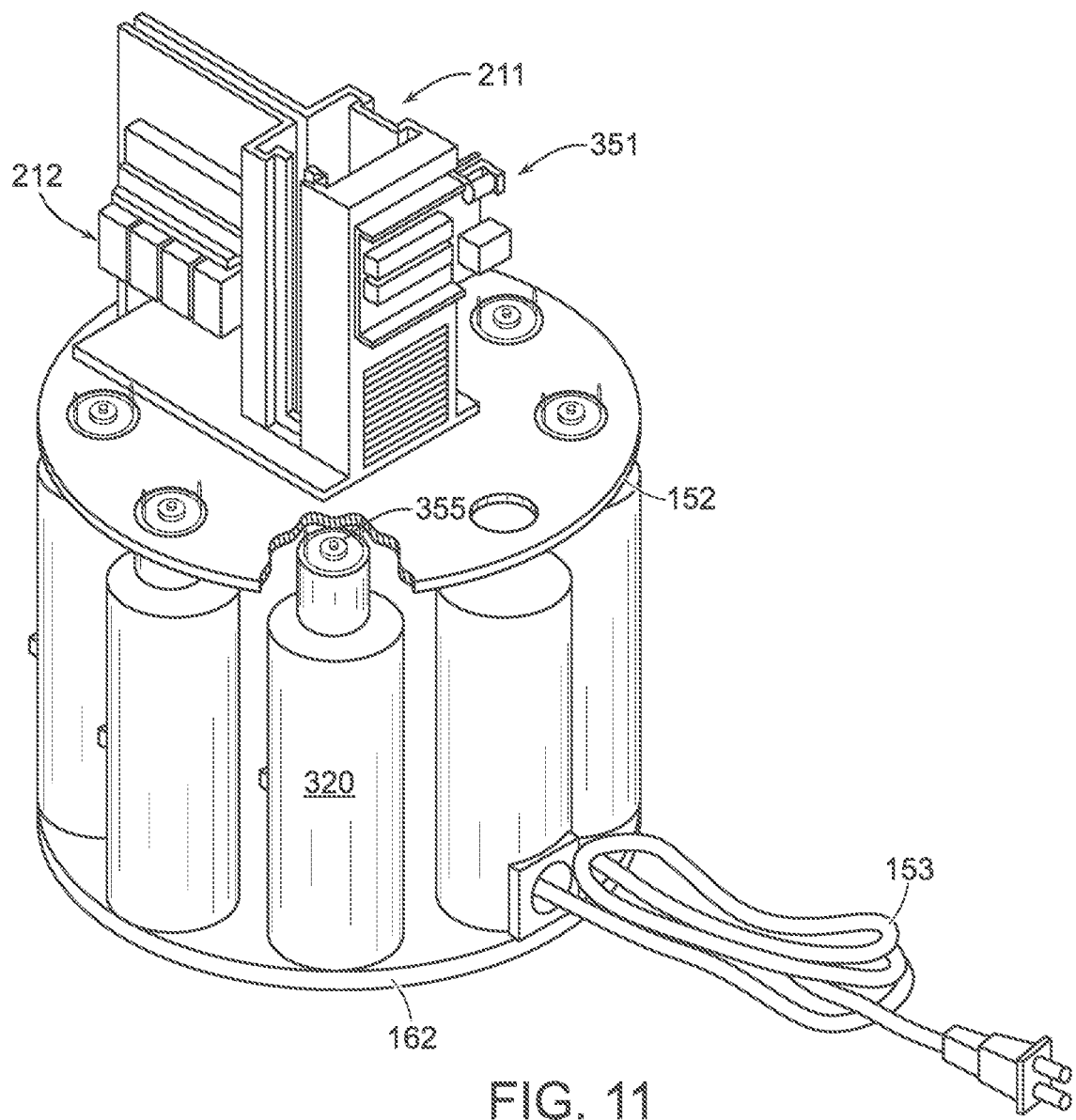
FIG. 11 is an isometric rendering of the top portion of an embodiment of the formulation device.

FIG. 11 shows one configuration of the assembled device with motors, relays, and microcontrollers exposed without the circuit housing 150. The structure is made of two flat round plates 152 and 162 covering the tops and bottoms of the plurality of pigment containers 320. The plurality of pigment assemblies 320 are arranged radially about the center. The top plate 152 provides mounting points for the plurality of pump motors 335 and electronics assembly. A two-prong plug 153 is displayed, but a three-prong grounded plug can be used as well.

Figure 12:
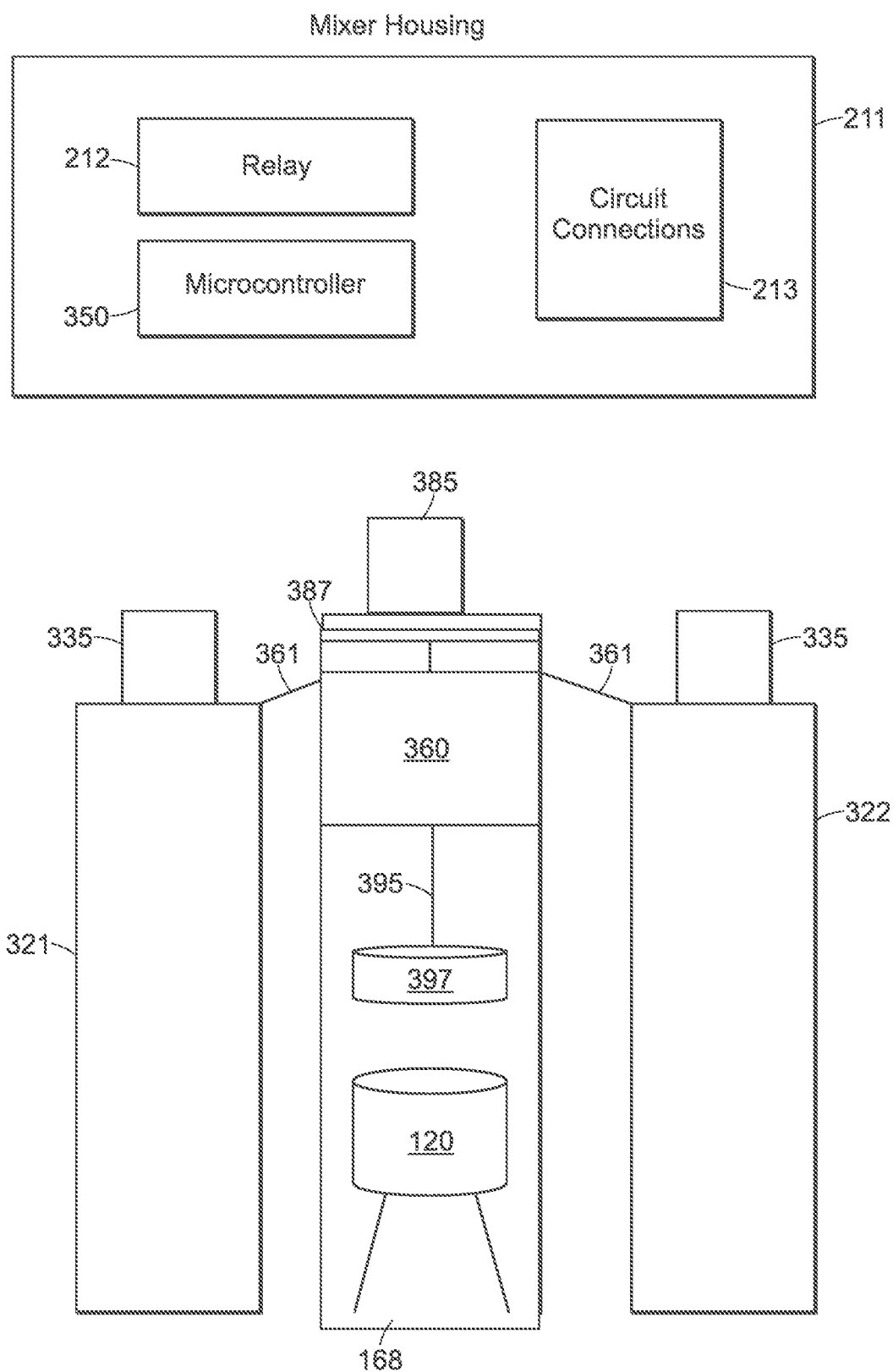
FIG. 12 is a plan view of a portion of an embodiment of the single batch formulation device.

FIG. 12 shows a plan view of a portion of an embodiment of the formulation device, including a mixer housing 211 that includes a microcontroller 350, relay 212, and circuit connections 213. The microcontroller 350 receives instructions as described in FIG. 4. The single batch formulation device 100 is configured to be in electronic communication with a remote interface device 200. A user inputs the selection of the type of cosmetic product and the color selection to the single batch cosmetic device by way of the remote interface device 200. Upon receiving the output signal 280, the relay 212 switches pump 340 in a pigment assembly 321 according to instructions sent by the microcontroller 350. Pigment is dispensed through tubing 333, 361 connected through dispensing head 360 to dispensing tips 367. The amount of pigment dispensed into the threaded container 120 depends on the amount of time allocated for the relay 212 to be open or closed. The relay 212 also controls pump motors 335 to control the dispensing of the pigment with the amount of pigment dispensed determined by the amount of time the relay turns the pump 340 on. The circuit connection 212 is for all internally connected circuitry including motors 335, 385, relays 212, and the microcontroller 350.

The homogenizer assembly 380 includes a mixer motor 385, a mixer height adjuster 387, a pigment mixing rod 395, and a homogenizer tip 397. The mixer housing 211 includes a mixer height adjuster 387 that lifts the mixer into the housing 211 when not in use. The mixer lowers the homogenizer tip 397 into the container 120 when in use. The container 120 initially contains base product 160 and pigment is dispensed directly into the container 120 by the dispensing head 365. The container 120 is manually placed on a stationary platform 165 before initiating customization.

Figure 13:
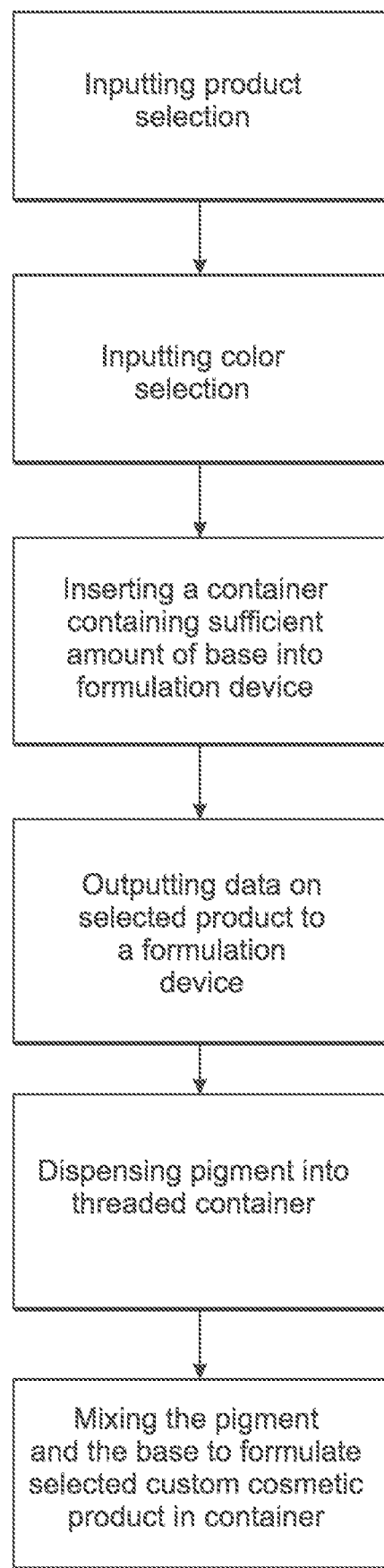
FIG. 13 is a general flow chart of the present process.
Figure 14:
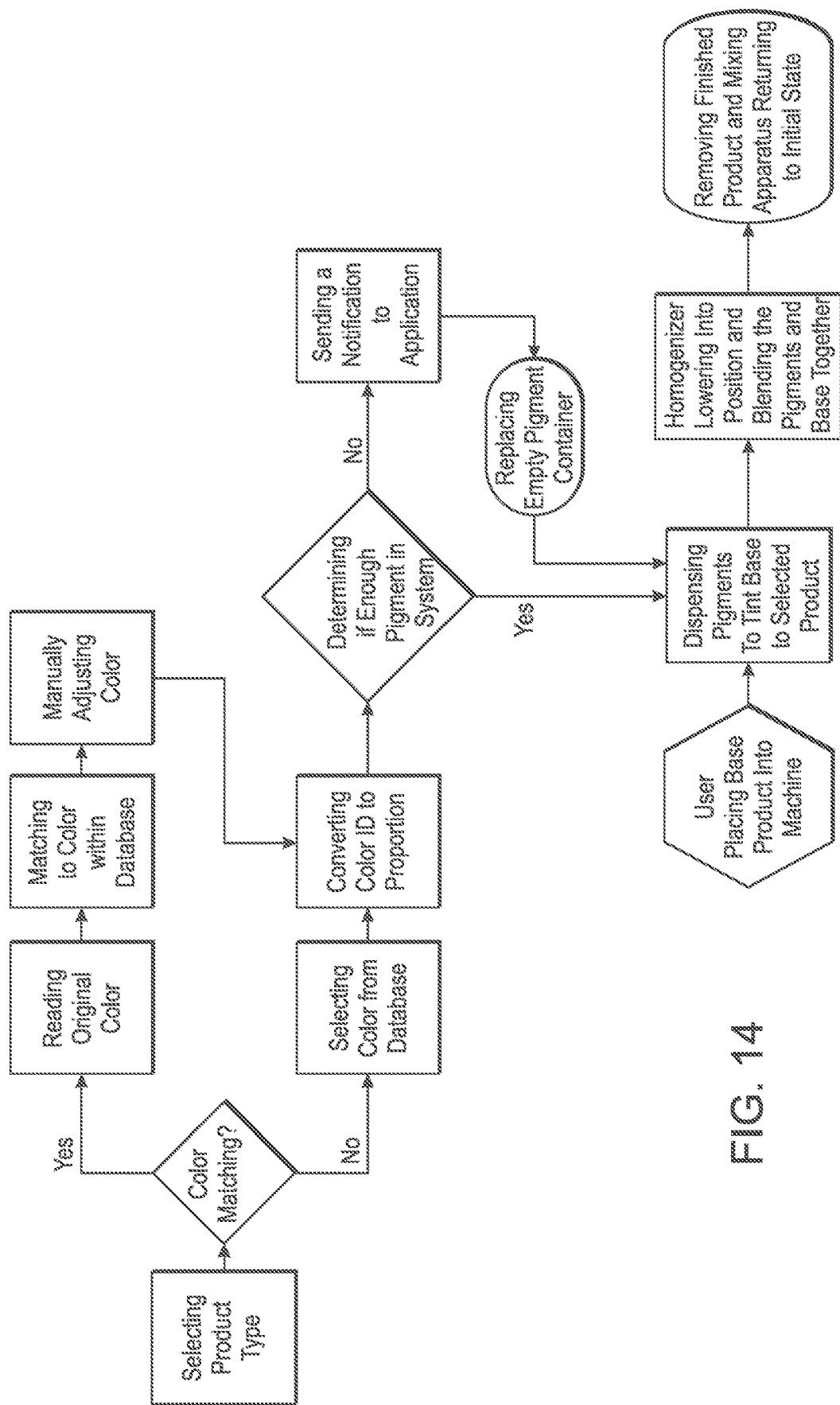
FIG. 14 is a detailed flow chart of the present process.

Now referring to FIGS. 13-14, a flow chart of the method is shown. The user selects a base product for the desired cosmetic product. A threaded container 120 contains between 8-15 mL of the base product. The threaded container 120 is inserted into the single batch formulation device 110. At this point, the user selects which product they are formulating in-app and chooses whether to select or match a color. If matching a color is chosen, the computer application 207 reads a color from an input, such as an image provided by the user. The color is matched to a color within the application's color database. The user is then able to manually adjust the color. If color selection is chosen, the user selects a color from the application's color database. The chosen color, whether from color matching or selection, is converted into a value that the device uses to create the desired shade. Upon initiation of the formulation process, the device determines whether or not there is enough pigment in the system. If there is not enough pigment, the formulation device 110 sends a notification to the interface device 200, notifying the user in the application 207 that the pigment container needs to be replaced. If the device determines there is enough pigment, the docking station locks, preventing the user from removing the threaded container during the color addition and cleaning processes. Pigment is dispensed to tint the base product to the selected color. A homogenizer lowers into position and blends the pigment and base together. Additionally, internal heating within the single batch formulation device assists with the mixing process. After completion, the mixing apparatus is returned to initial state, and the user can remove the finished product.

The base product for lip gloss can include: emollients, colorants (pigment), thickening agents, and other additives such as fragrance or flavoring agents. Control agents can also be added to combat microbial growth. In one exemplary embodiment the threaded container 120 for lip gloss includes: Hydrogenated Polyisobutene,(and),Ethylene/Propylene/Styrene,Copolymer,(and) Butylene/Ethylene/Styrene Copolymer; Micronized Titanium Dioxide; a plurality of waxes: beeswax, carnauba, sumac wax, candelilla wax, ozokerite; a plurality of oils: lanolin, polybutene, almond, coconut, avocado, jojoba, castor oil, linseed oil, sesame oil, shea butter, and silicone-based oils. The base product can be either a white-based product to have color added, or the white pigment of the single batch device 110 to provide the proper proportions of white in a certain shade (with the base product being a translucent mixture). The base product for nail polish can include: polymers dissolved into a volatile, organic solvent, nitrocellulose dissolved in butyl acetate or ethyl acetate. Common ingredients also include: plasticizers (prevent brittleness), dyes and pigments, opalescent (enhance coloration), adhesive polymers (ensure nitrocellulose adheres to surface of nail), thickening agents (prevent premature settling of pigments), and ultraviolet stabilizers (resist color change when exposed to sunlight). In one exemplary embodiment, the threaded container 120 for nail polish includes: Butyl Acetate, Ethyl Acetate, Nitrocellulose, Adipic Acid/Neopentyl Glycol/Trimellitic Anhydride Copolymer, Acetyl Tributyl Citrate, Isopropyl Alcohol, Acrylates Copolymer, Stearalkonium Bentonite, N-Butyl Alcohol, Styrene/Acrylates Copolymer, Benzophenone-1, Silica, Alumina, Trimethylpentanediyl Dibenzoate, Micronized Titanium Dioxide, and a choice of oil. The base product for the foundation can include: oils and emollients, water, silicone (dimethicone, polysiloxane, etc.), oils, and colorants. In one exemplary embodiment, the base product for foundation can include: Water, emulsifying ingredients such as Dimethicone Crosspolymer or Polysilicone-11, Titanium Dioxide, Iron Oxides, viscosity controlling ingredients such as Isohexadecane and Cyclomethicone, mineral clays such as Silica or Kaolin, emollients such as Glycerin or Squalane, and Natural Preservatives.

While the invention has been described with reference to preferred and example embodiments, it will be understood by those skilled in the art that a variety of modifications, additions, and deletions are within the scope of the invention, as defined by the following claims.

We claim:

1. A single batch formulation device configured to formulate a customized cosmetic product comprising:
    a bottom plate supporting the single batch formulation device;
    a plurality of pigment assemblies positioned above the bottom plate wherein each of the pigment assemblies is comprised of a pigment container connected to a pump and pump motor wherein the pigment container contains a pigment ingredient correlating with a specific color;
    a recessed area wherein the plurality of pigment assemblies is positioned around the recessed area;
    a dispensing assembly comprised of a dispensing head and a plurality of dispensing tips, wherein each of the plurality of dispensing tips is in a direct fluid connection with one of the plurality of pigment assemblies;
    a homogenizer assembly comprised of a mixing motor connected to a pigment mixing rod wherein the pigment mixing rod is disposed below the dispensing assembly and the pigment mixing rod is positioned within the recessed area;
    a stationary platform positioned within the recessed area wherein the pigment mixing rod is of sufficient length to contact a base product contained in a container positioned on the stationary platform; and a micro-controller configured to control the operations of the single batch formulation device.

2. The single batch formulation device of claim 1 wherein each of the pigment assemblies is comprised of a peristaltic pump in fluid connection with the pigment container, the peristaltic pump comprised of a plurality of rollers.

3. The single batch device of claim 1 further comprising: a top plate, wherein the plurality of pigment assemblies is positioned below the top plate.

4. The single batch device of claim 1 further wherein the homogenizer assembly further comprises a mixer height adjuster, the mixer height adjuster attached to the mixing motor.

5. The single batch device of claim 1 further comprising: a computer application deployed on an interface device to facilitate a cosmetic product selection and a color selection.

6. The single batch device of claim 1 further comprising: a micro-controller configured to control the operations of the single batch formulation device a remote interface device is in electronic communication with the single batch formulation device, and wherein the remote interface device is configured to input the selection of the cosmetic product and the color selection to the single batch cosmetic device, and a plurality of containers, each container of the plurality of containers sized to be imported into the single batch formulation device, and each of the containers containing a base specific for a type of cosmetic product of the plurality of cosmetic products, wherein the single batch formulation device is configured to formulate the cosmetic product to a selected color and export the cosmetic product into one of the plurality of containers.

7. The system of claim 1, wherein the system further comprises a lid to mate with the container.

8. The system of claim 1, wherein the cosmetic product is selected from the group consisting of: foundation, lip gloss and nail polish.

9. The system of claim 1, wherein the cosmetic product is foundation, wherein the base is comprised of: oils, emollients, water, silicone, and colorants.

10. The single batch device of claim 1, further wherein the plurality of pigment assemblies are arranged radially about the center of the recessed area below the top plate.

* * * * *